United States Patent
Sidman et al.

(10) Patent No.: US 9,877,658 B2
(45) Date of Patent: Jan. 30, 2018

(54) PASSIVE METHOD AND SYSTEM FOR CONTACT AND/OR NON-CONTACT WITH OR WITHOUT INTERVENING MATERIALS FOR DETECTION AND IDENTIFICATION OF THE INCIDENCE, TRAVERSE AND PHYSIOLOGICAL CONDITION OF A LIVING HUMAN AT ANY INSTANT

(71) Applicant: DKL INTERNATIONAL, INC., Reston, VA (US)

(72) Inventors: Howard B. Sidman, Vienna, VA (US); Robert Van Dine, Mountoursville, PA (US); William H. Hutson, Little Compton, RI (US)

(73) Assignee: DKL INTERNATIONAL, INC., Reston, VA (US)

( * ) Notice: Subject to any disclaimer, the term of this patent is extended or adjusted under 35 U.S.C. 154(b) by 169 days.

(21) Appl. No.: 14/590,797

(22) Filed: Jan. 6, 2015

(65) Prior Publication Data

US 2016/0120413 A1    May 5, 2016

Related U.S. Application Data

(60) Provisional application No. 62/072,288, filed on Oct. 29, 2014.

(51) Int. Cl.
| | |
|---|---|
| *G08B 23/00* | (2006.01) |
| *A61B 5/0205* | (2006.01) |
| *A61B 5/0428* | (2006.01) |
| *A61B 5/00* | (2006.01) |

(52) U.S. Cl.
CPC ........ *A61B 5/0205* (2013.01); *A61B 5/04282* (2013.01); *A61B 5/04284* (2013.01); *A61B 5/6887* (2013.01); *A61B 5/7207* (2013.01); *A61B 2503/045* (2013.01); *A61B 2562/0257* (2013.01)

(58) Field of Classification Search
CPC .... G08B 21/0453; A61B 5/02; A61B 2503/00
USPC ........ 340/573.1, 552, 551, 561, 657; 702/65
See application file for complete search history.

(56) References Cited

U.S. PATENT DOCUMENTS

| | | | |
|---|---|---|---|
| 5,748,088 A | 5/1998 | Afilani | |
| 5,907,280 A | 5/1999 | Afilani | |
| 6,011,476 A * | 1/2000 | Afilani | ................... G01N 27/60 324/452 |
| 6,078,179 A | 6/2000 | Afilani | |

(Continued)

OTHER PUBLICATIONS

Hutson, William H., "Transfer Functions Under No-Analog Conditions: Experiments with Indian Ocean Planktonic Foraminifera," Quaternary Research, vol. 8, 1977, pp. 355-367.

*Primary Examiner* — Phung Nguyen (74) *Attorney, Agent, or Firm* — Nixon & Vanderhye P.C.

(57) ABSTRACT

A low input current amplifier has a voltage spectral density curve to operate at 50 Hz or less and is connected to dielectric materials to receive a signal irrespective of ground reference. The amplifier outputs a first output. A multi-stage amplifier includes a stage connected in series with the low input current amplifier to amplify the first signal to distinguish the incidence, traverse and physiological condition of a living human. The resulting signal is then processed by an algorithm and displayed as human specific motion, heart rate and respiratory rate.

32 Claims, 12 Drawing Sheets

(56) References Cited

U.S. PATENT DOCUMENTS

| | | | |
|---|---|---|---|
| 6,161,070 A * | 12/2000 | Jinno | B60R 21/01532 |
| | | | 280/735 |
| 6,411,099 B1 | 6/2002 | Afilani | |
| 6,496,114 B1 | 12/2002 | Afilani | |
| 6,674,366 B1 | 1/2004 | Afilani | |
| 6,686,842 B1 | 2/2004 | Afilani | |
| 2014/0055269 A1 * | 2/2014 | Howie | A61B 5/04 |
| | | | 340/573.1 |
| 2015/0157269 A1 * | 6/2015 | Lisogurski | A61B 5/0205 |
| | | | 600/301 |

* cited by examiner

PASSIVE METHOD AND SYSTEM FOR CONTACT AND/OR NON-CONTACT WITH OR WITHOUT INTERVENING MATERIALS FOR DETECTION AND IDENTIFICATION OF THE INCIDENCE, TRAVERSE AND PHYSIOLOGICAL CONDITION OF A LIVING HUMAN AT ANY INSTANT

CROSS-REFERENCES TO RELATED APPLICATIONS

This application claims the benefit of U.S. Provisional Patent Application Ser. No. 62/072,288, filed Oct. 29, 2014, the entire content of which is herein incorporated by reference.

STATEMENT REGARDING FEDERALLY SPONSORED RESEARCH OR DEVELOPMENT (Not Applicable)

BACKGROUND AND SUMMARY OF THE INVENTION

The present invention relates to a method and system for the passive detection and classification of human specific signals (HSS) originating from the incidence, traverse and physiological conditions of a living human. The disclosures of commonly-owned U.S. Pat. No. 6,686,842 and U.S. Pat. No. 6,011,476 are hereby incorporated by reference.

Figure 1:
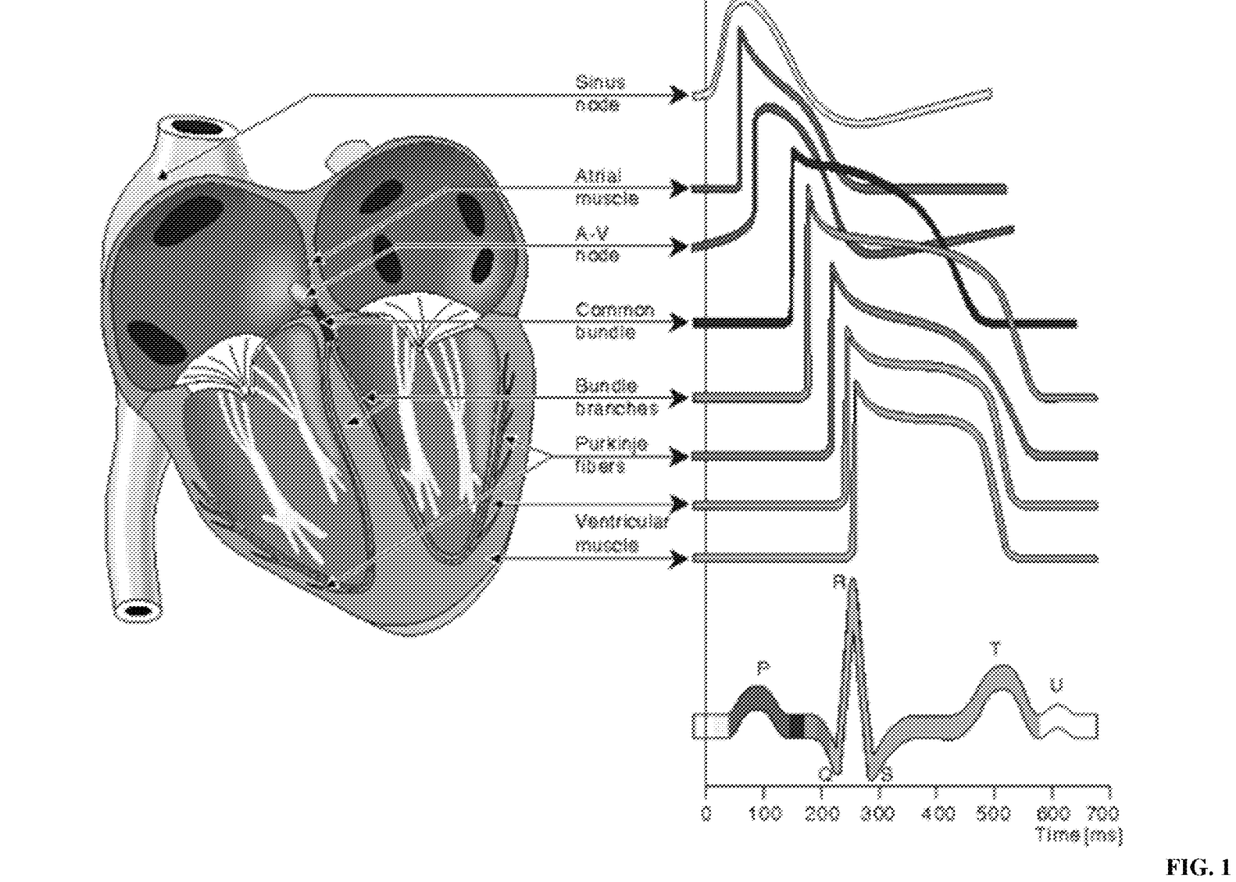
FIG. 1 is a simplified human heart locating the major sources of the electrical cardiac activity and the discrete electrical activity forming the PQRST amplitude signal.

The method identifies electric field patterns of the living human, which contains all components of the living human physiological functions. Human Electric Field is in the ULF (1-2 Hz) range and extremely non-uniform. The electric field varies greatly in magnitude, space and vector direction. Amplitude variations form the ECG pattern detected on the surface of the skin. The major source of the electric field is the polarization, rapid depolarization and repolarization of the heart. FIG. 1 is a simplified human heart locating the major sources of the electrical cardiac activity and the discrete electrical activity forming the PQRST amplitude signal.

The human heart generates on the surface of the living humans skin, a coherent dynamic pulse that is refreshed approximately every second. The PQRST pulse is a superposition of several Delta function impulses. The QRS portion has a voltage of about 1.8 mV across a cell membrane of less than a micron with duration of 0.06-0.1 seconds. This equates to an electric field strength of $10^6$ volts per meter and is very large in relation to the natural environment. The Spatial change and the delta function of the action potentials at this point create extremely large volts per cm per cm per second change in the electric field. It is a matter of this invention to passively and without contact to detect and separate signal components of this electric field and to provide alerts to changes in the electric field which may or may not be considered abnormal. The respiration signal results from the movement of polarized lung and muscle tissue concomitant with inhalation and exhalation.

BRIEF DESCRIPTION OF THE DRAWINGS

These and other aspects and advantages will be described in detail with reference to the accompanying drawings, in which.

DETAILED DESCRIPTION OF THE INVENTION

Figure 2:
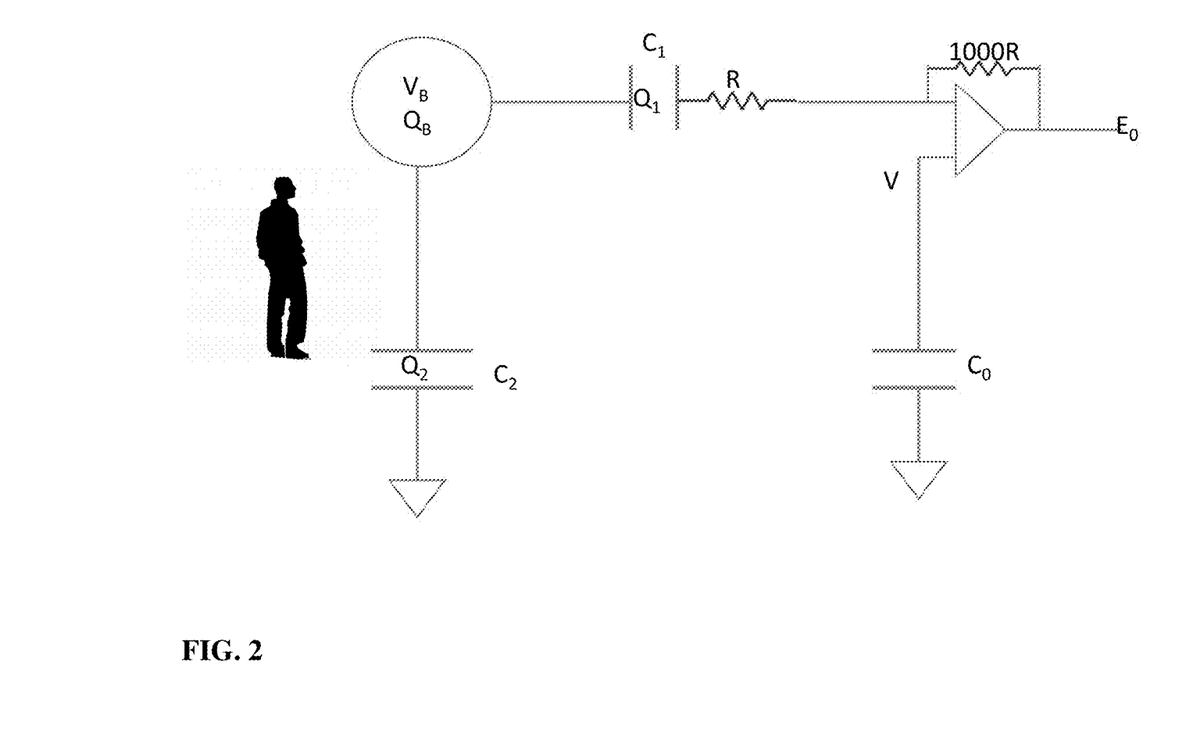
FIG. 2 is a simplified model circuit representation of detecting the living human.

A simplified model circuit representation of detecting the living human is shown in FIG. 2 where:

VB=static voltage of the body
QB=static charge on the body
C1=capacitance between sensor and body
C2=capacitance between body and the earth
C0=capacitance between ground of amplifier and earth
V=voltage at input to amplifier
Q1=charge on C1
Q2=charge on C2
Eo=Output In the case of detecting the presence or traverse of the living human. C2 dominates. In the case of the physiological condition of the living human, C1 dominates. That is, by "dominates," the amplitude of the traveling voltage wave generated between the living human and local ground is significantly larger than the travel voltage wave generated between the polarized tissue and organ planes of living human's physiological function. In either case, the human electric field is detected in a passive mode and without differential signal inputs.

The present invention is a method and system for monitoring the spatial dynamics of a polarized (volts/meter) entity including tissue, organs and the living body. At distances of meters, the traverse/movement of the polarized body generates the spatial dynamics expressed as volts/m/second, the traveling voltage gradient (i.e., C2 dominates). At close distances, decimeters to centimeters, it is tissue and/or organs that generate the spatial dynamics and the propagation of the traveling voltage gradient (i.e., C1 dominates). The sensor is a multi-purpose, very low frequency sensor capable of responding to a wide variety of electromagnetic sources, and providing a digital output for signal processing and display.

The sensor has three separate sensing input conditions and is optimized to detect "Traveling Voltage Gradient" (TVG), "Magnetic Field" (M-Field), or "Electric Field" (E-Field) signals.

Figure 3:
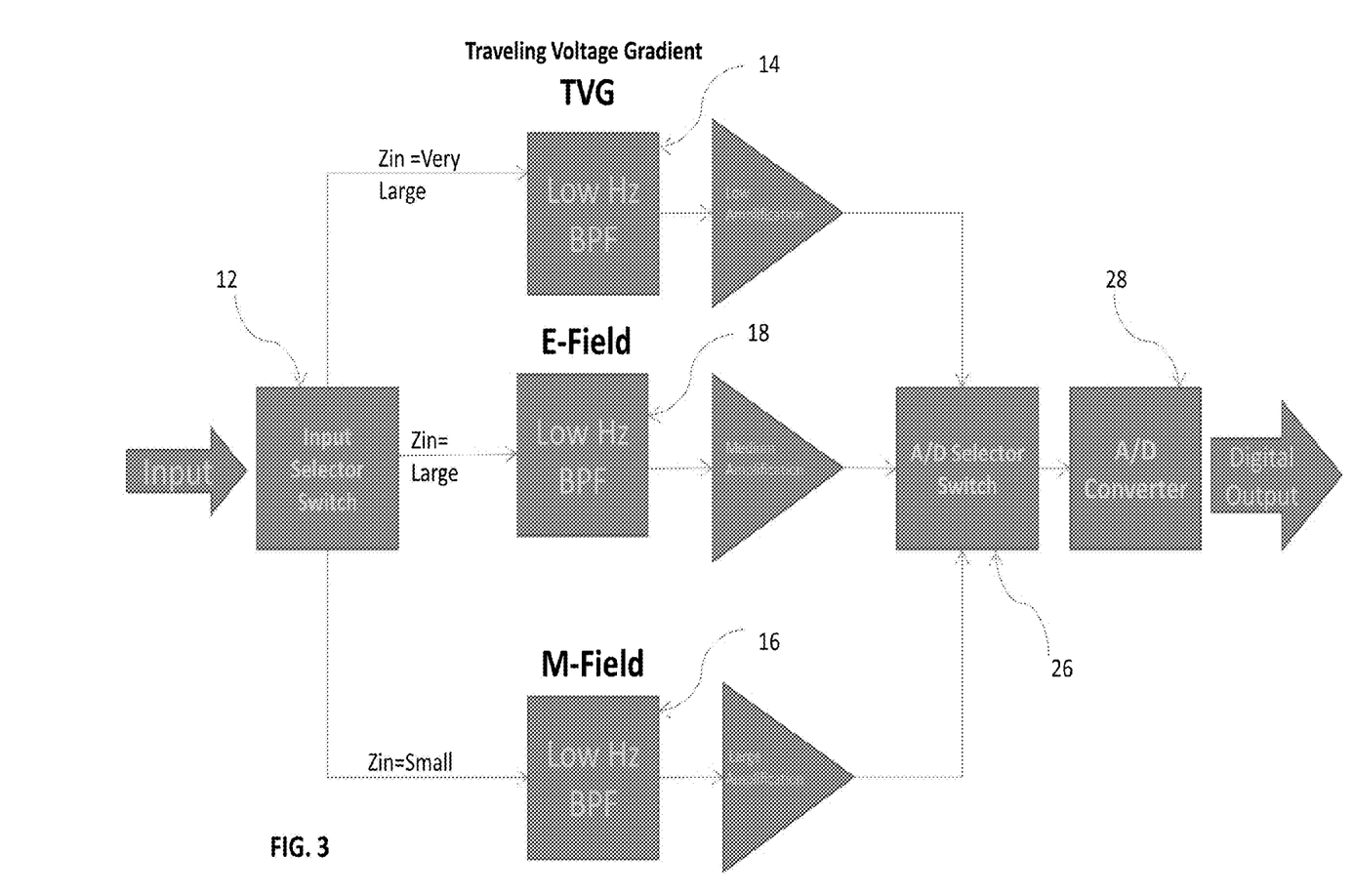
FIG. 3 is a functional diagram.

FIG. 3 is a functional diagram. All circuits are optimized to sense very low frequency signals, e.g., 50 Hz or less, having bandpass filters (BPF) optimally passing only low frequency. Extraneous ambient electromagnetic background noise, such as power line noise, is greatly attenuated. All circuits operate as a null detector in that they zero to the background volts/meter. From the zeroed state, the circuit detects and provides a digital output for quantifying the amplitude changes. These changes are then processed and displayed.

An input selector switch 12 is operator controlled and is selected based on the desired field to analyze and the data being collected. That is, the operator may selectively collect data from the TVG (position 1), which is presented as volts, or measuring the electric field (position 2) as a change in microvolts or lower, or measuring the change in the magnetic field (position 3) in milliamperes or lower.

The TVG 14 has very high impedance (Zin), which allows ultra-sensitive TVG stimulus detection producing a voltage-based signal with a single-conductor sensor of application optimized length and surface area. The circuit is detecting and quantifying the amplitude of the volts per meter per second (the acceleration of the electric field).

The "M-Field" 16 is very low impedance, optimized to detect currents generated by a changing magnetic field.

The "E-Field" 18 has a large input impedance, being a general-purpose circuit with the characteristic impedance of free space, akin to radio front ends, with a very-low frequency sensor. It produces a voltage based signal.

For the TVG circuit 14, a low input current amplifier having a low frequency voltage spectral density curve (e.g., 50 Hz or less) is electrically connected to conductive dielectric materials which are proximate to or in contact with the living human or in contact with intervening dielectric materials proximate to or in direct contact with the living human. Exemplary dielectric materials include porcelain (ceramic), mica, glass, plastics, and the oxides of various metals, and the like. Some liquids and gases can serve as good dielectric materials. Dry air is an excellent dielectric and is used in variable capacitors and some types of transmission lines. Distilled water is a fair dielectric, and a vacuum is an exceptionally efficient dielectric. The circuit is designed to detect and amplify low level currents induced on the collector by changing electric or magnetic fields or by changes in the traveling voltage gradient. These changes result in a very low level current on the collector as a result of the changes in E and M field and TVG in relation to the ambient conditions. The current circuit is not limited to the current design and may change based on the target detection material, but the circuit designs are preferably low pass and with a spectral density curve of 50 Hz or less.

Figure 4:
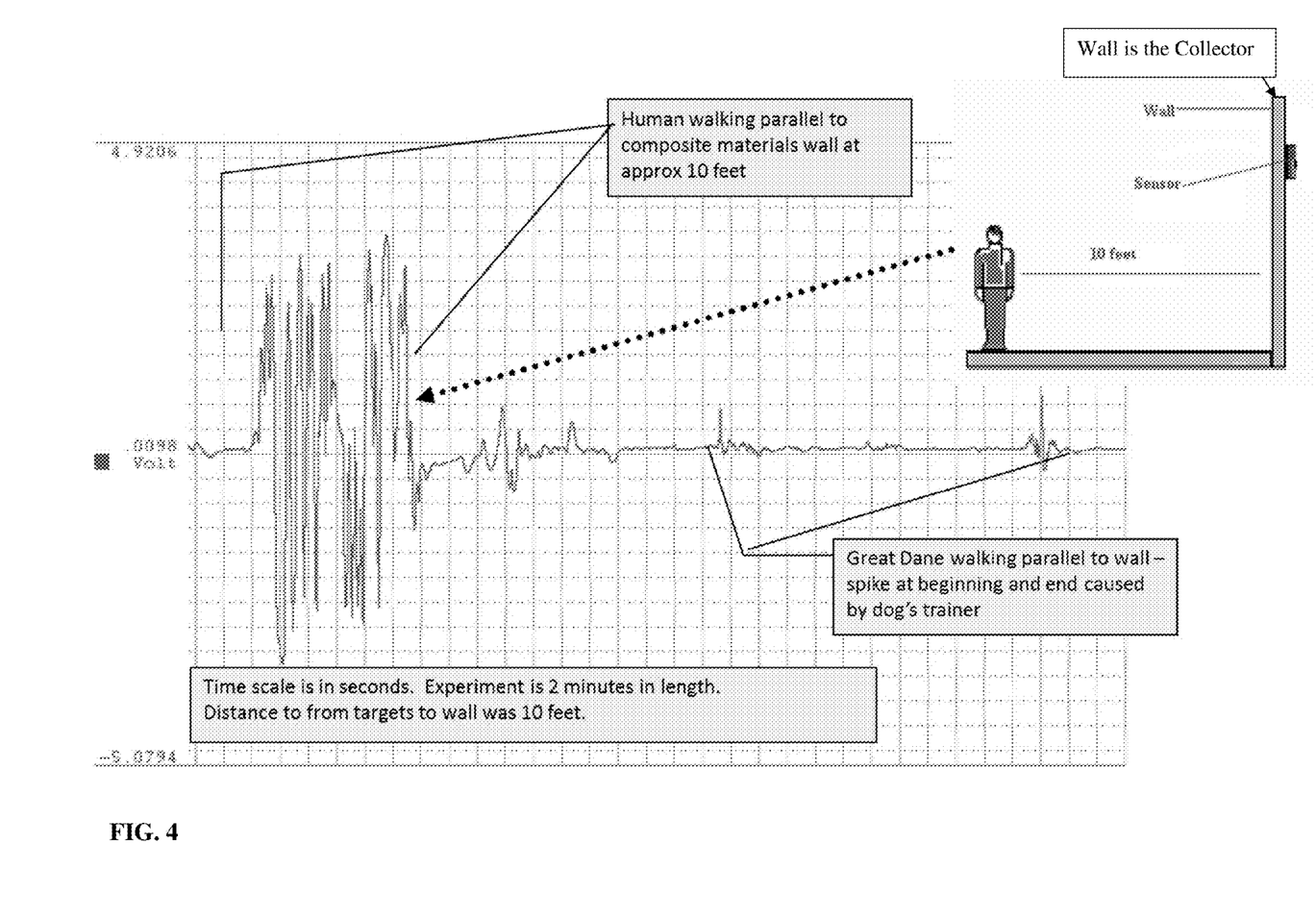
FIG. 4 is a typical system including the collector and amplifier.

The system responds to low frequency changes in the volts per meter pattern on the collector conductive dielectric materials. That is, the system indicates a change in the TVG that is sufficient to make a change in the output of the system. The collector conductive dielectric materials may be the intervening dielectric materials or the proximate/in-contact dielectric materials. The "collector" relates to the conductive dielectric material that is electrically connected to the amplifier. The collector is a conductive dielectric material and may be contact or contactless. Exemplary conductive dielectric materials for the collector may include TIVAR plastic, Mylar (as an example of flexible material), composite construction plywood in the wall (as shown in FIG. 4), coaxial cable (used in the traverse situation), and others. In proximate detection the intervening dielectric may be air, clothing or a door or the like. As the volts per meter pattern changes, the system characterizes the change and instantaneously resets and responds to the succeeding (i.e., next) voltage pattern change. The system is passive. No reference or differential signal is created or emitted by the system.

For the E-field circuit, a low input current amplifier having a low frequency voltage spectral density curve that preferably operates at 50 Hz or less is electrically connected to conductive dielectric materials, the collectors, which are proximate to, in contact with the living human or in contact with intervening dielectric materials proximate to or in direct contact with the living human. Examples of dielectric materials that are suitable include various plastics and inks that are more conductive than the environment they are placed in. An exemplary ink is DuPont 5025. The system responds to low frequency (e.g., 50 Hz or less) changes in the electric field on the collector dielectric materials. As the electric field changes, the system instantaneously resets and responds to the succeeding changes. The system is passive. No reference or differential signal is created or emitted by the system.

For the M-field circuit, a low input current amplifier having a low frequency spectral density curve that preferably operates at 50 Hz or less is electrically connected to conductive dielectric materials, the collectors, which are proximate to, in contact with the living human or in contact with intervening dielectric materials proximate to or in direct contact with the living human. Examples of suitable dielectric materials are various plastics and inks that are more conductive than the environment they are placed in. The system responds to low frequency (e.g., 50 Hz or less) changes in the magnetic field on the collector dielectric materials. As the magnetic field changes, the system instantaneously resets and responds to the succeeding changes. The system is passive. No reference or differential signal is created or emitted by the system.

The A/D selector switch 26 is an analog multiplexor that automatically routes the analog signal to an A/D converter 28 depending on which input is selected by the operator. The A/D converter 28 converts the continuous physical/analog voltage or current to a digital number that represents the physical/analog voltage or current's amplitude.

FIG. 4 indicates a typical system including the collector (e.g., wall in FIG. 4) and amplifier, wherein the system is in contact with dielectric wall materials at a distance of 10 feet from the parallel traverse of a living human and sequentially a large Great Dane dog. During a period of 2 minutes, the system raw amplitude signals within the output range of +/−5 volts indicates presence and traverse of the living human. The amplitude signals of the dog are significantly less.

Figure 5:
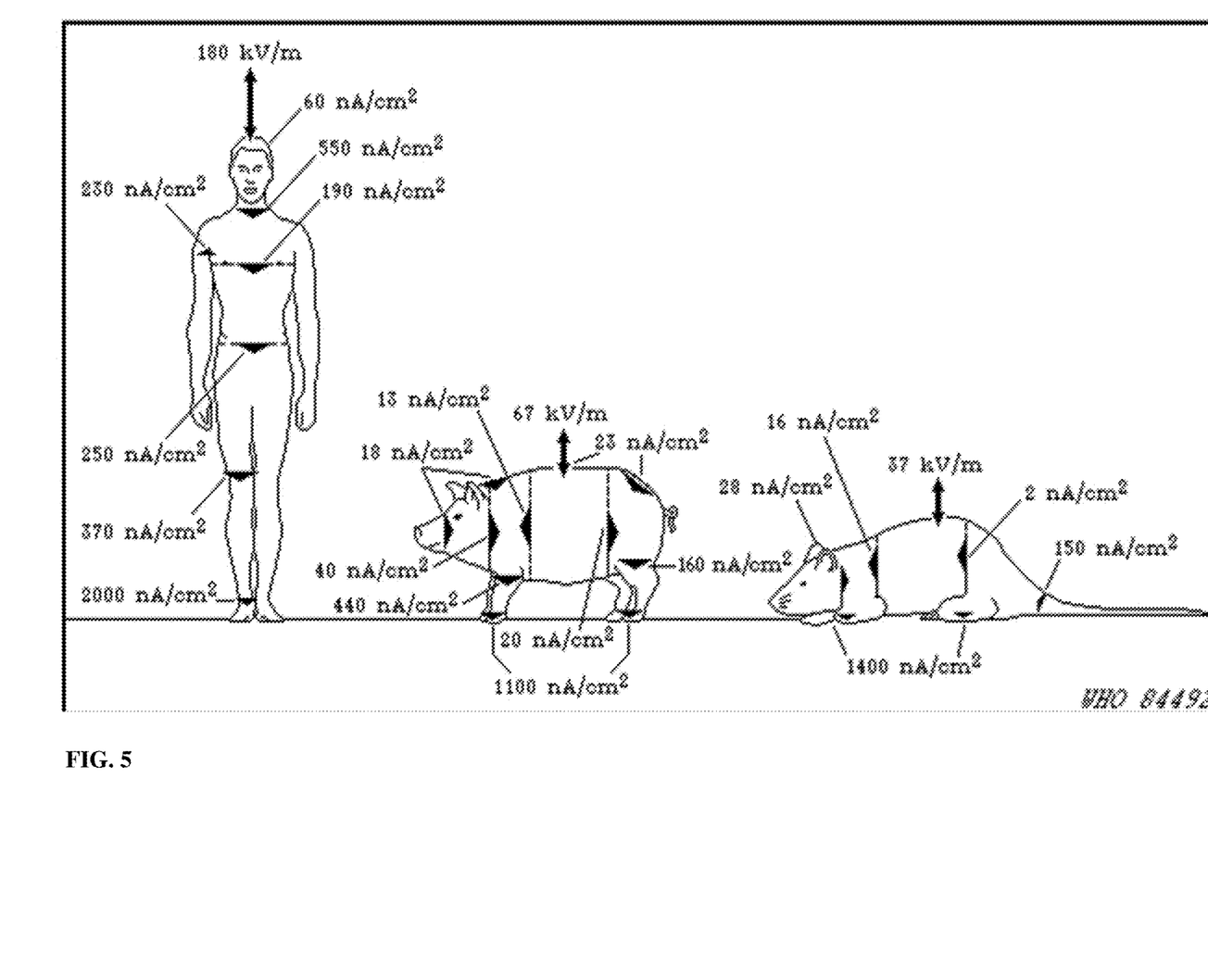
FIG. 5 shows electric field strengths of various entities.

The raw amplitude voltage signal displayed in FIG. 4 classifies by voltage amplitude the presence and traverse of the living human in contrast with the large dog. The voltage per meter pattern collected on the dielectric wall materials results from the naturally occurring higher electric field strength shown in FIG. 5 of the living human at 180 kV/m in contrast to a porcine at 67 kV/m and the smaller rodent at 37 kV/m.

Figure 6:
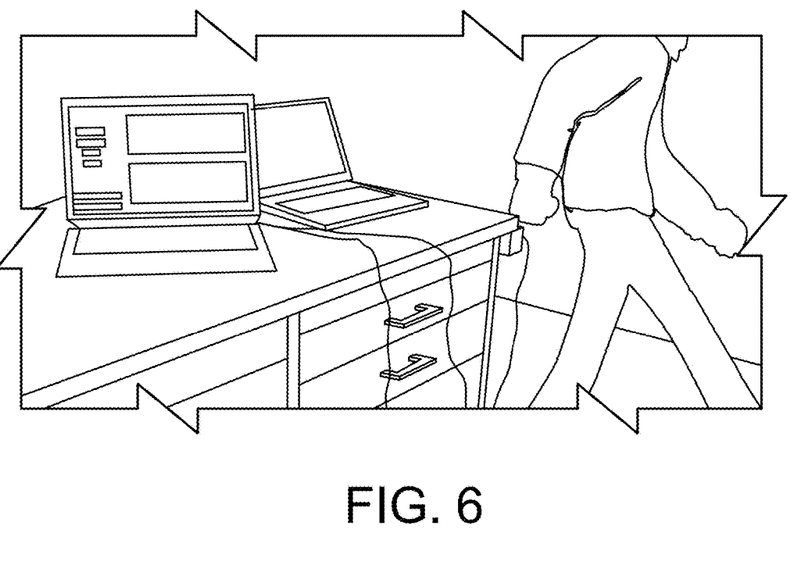
FIG. 6 shows a human traversing a collector.

In another embodiment shown in FIG. 6, a human traverses a collector which is a 2 feet by 2 feet square of commercial carpet. The carpet is placed on the floor. The carpet is connected to the collector of the amplifier circuit. During a period of 2 minutes, the human traverses the collector several times. The raw amplitude voltage pattern output of the amplifier circuit (+/−5 volts) indicates the human traversing the carpet and collector.

Figure 7:
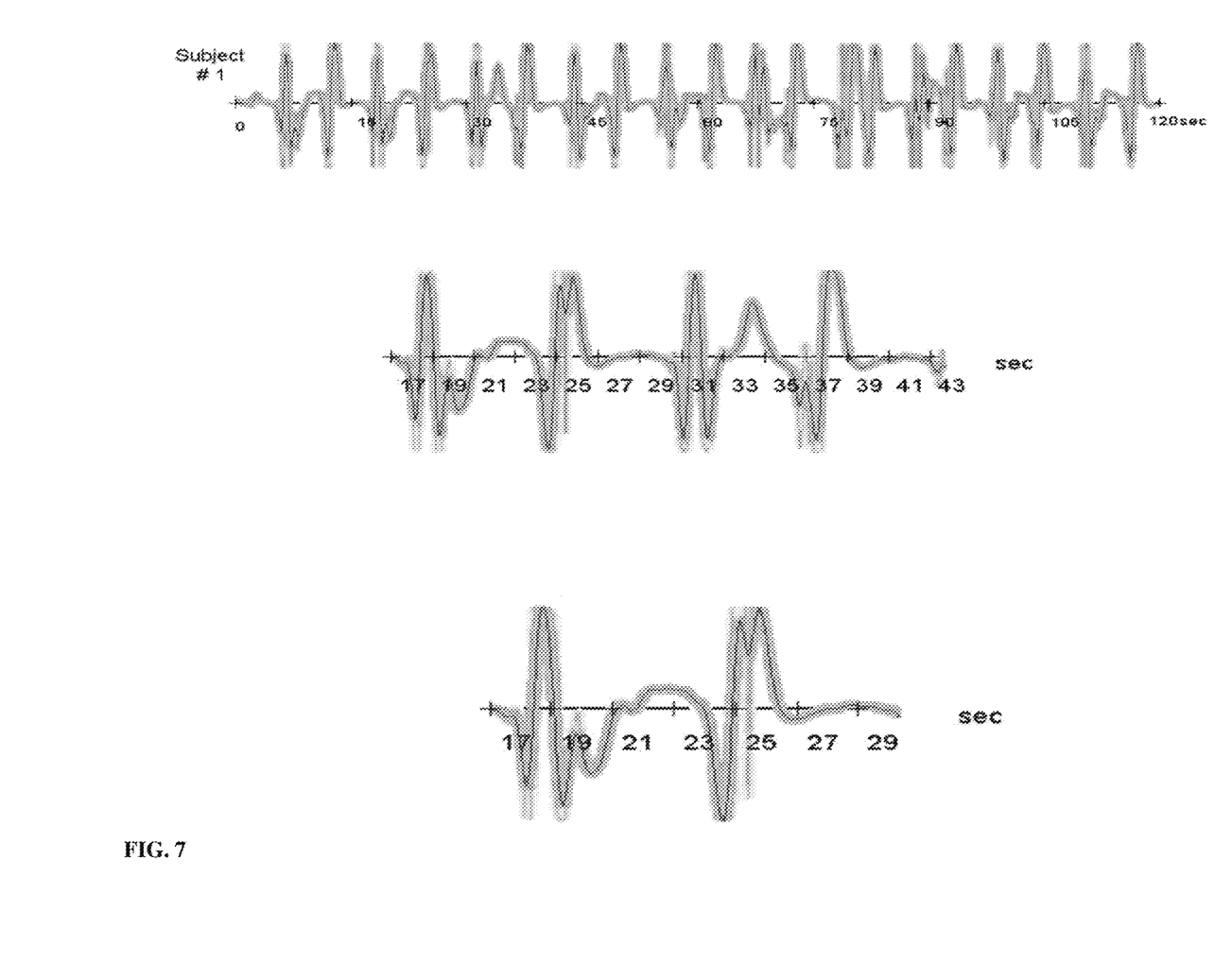
FIG. 7 shows various voltage amplitude patterns of an adult human traversing the collector.

The voltage amplitude pattern output of the embodiment in FIG. 6 indicates the presence and traverse of the human across the carpet and collector arrangement. In FIG. 7, the top display shows the repeatability of the human specific signals (HSS). The middle display shows the HSS in expanded detail, and the voltage pattern indicates the direction of crossing. The bottom display is enlarged to show the difference in the signals resulting from the human traversing the collector in opposite directions.

Further, the system processing algorithm categorizes the voltage signal pattern (signal) such as the above according to human and non-human groups (non-human living entity) in three steps. The first step is grouping, where signals are acquired from the sensor that span the variability of signals to be detected and classified. These signals are established by repetitive experiments which are controlled and recorded. The signals are then separated in two or more groups which represent the types of signals the system will encounter. The second step is calibration, where a series of operations are used to generate a set of filters which, when applied to the data, separate the signals into the groups of the first step. The third step is classification, where the filters generated in the second step are utilized and when applied to new signals, yield a set of numbers indicating the degree to which the sample correlates with each of the groups determined in the first step. The correlation between the set of filters and the signal data may be based on standard correlation techniques, such as the Pearson product-moment correlation coefficient, or variants. Another approach includes computing the multi-dimensional angle between filters and samples (cosine theta)—and similar techniques.

An alternate approach to classification is to compare the multi-dimensional distance between a sample and the filters generated in the second step. In this approach, the Mahalanobis distance between a sample and the filters may be calculated to determine the à priori probability of each sample belonging to the various groups, determined in the first step above. On the basis of these à priori probabilities, samples may be classified as belonging to one of a number of classes.

Other numerical approaches may be used to determine which group a sample belongs, as warranted. For example, a numerical process may be used to determine whether a sample falls within the scope of the calibration data described above, or falls outside the scope, indicating a "no-analogue condition;" that is, an incomplete calibration and potential misclassification of samples [see reference: "Transfer functions under no-analog conditions: Experiments with Indian Ocean planktonic Foraminifera," Hutson, William Halsey, Department of Geological Sciences, Brown University, Providence, R.I. 02912 USA; and School of Oceanography, Oregon State University, Corvallis, Oreg. 97331. Quaternary Research, Volume 8, Issue 3, p. 355-367. 11/1977].

Figure 8:
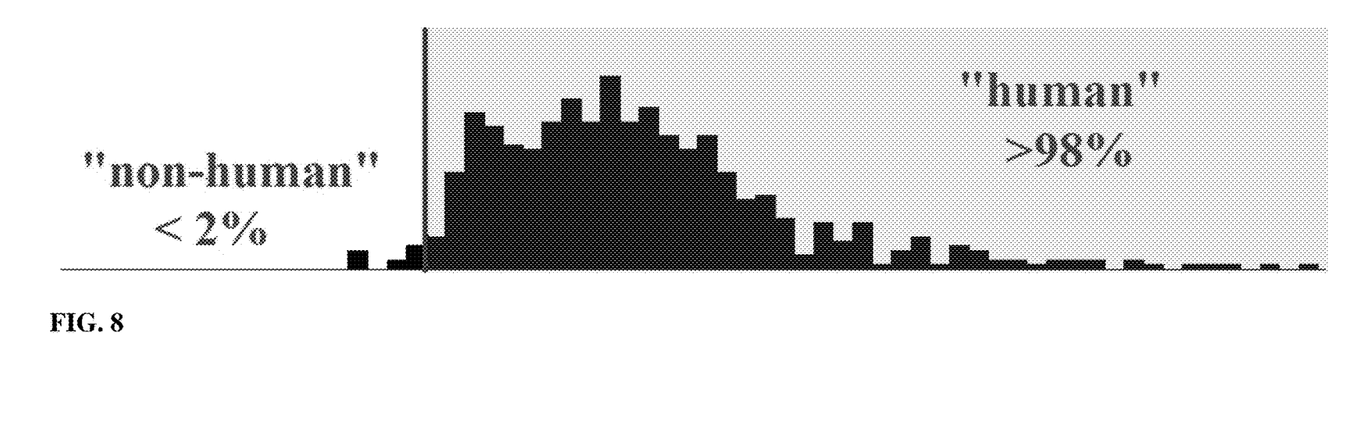
FIG. 8 is a histogram illustrating the performance of the algorithm in identifying and classifying human specific signals.

The method is capable of classifying human specific signals traversing the collector with accuracy above 98%. In 844 voltage patterns collected by a third party and divided into four groups: Noise, Inanimate, Animal and Human, the histogram shown in FIG. 8 illustrates the performance of the algorithm in identifying and classifying the human specific signals. The bars in the section marked "human" represent correctly identified human patterns. The bars in the section marked "non-human" indicate incorrect identifications of human voltage patterns. The performance of the processing algorithm in classifying voltage pattern according to human, and non-human are as follows (FIG. 8):

1. humans correctly identified as human (>98%)
2. humans incorrectly (false negative rate) dismissed as non-human (<2%)
3. non-humans incorrectly (false positive rate) identified as human (<4%)

This capability is useful for any environment where human presence or movement is valuable.

Figure 9:
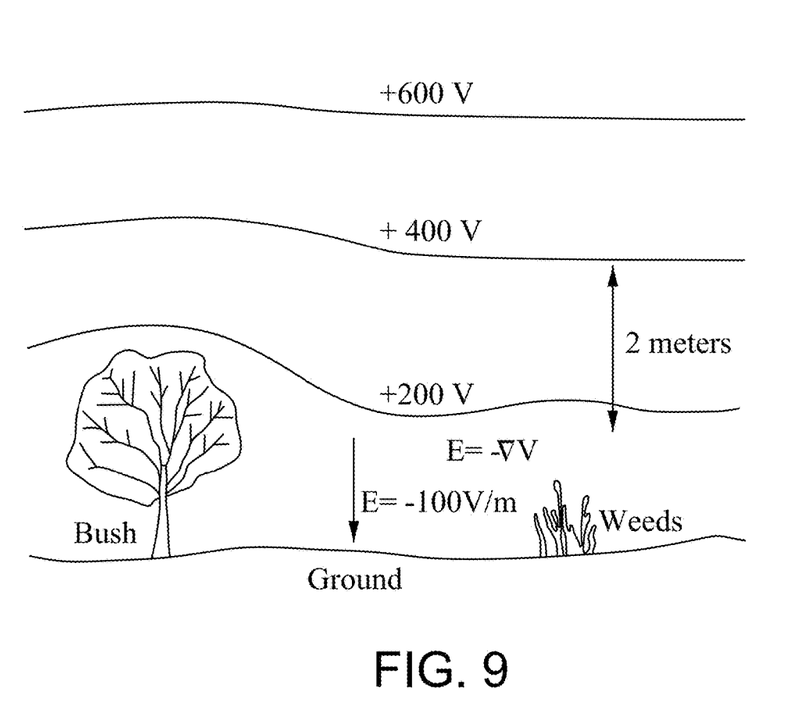
FIG. 9 shows an exemplary electric field of the Earth.

The changing electric field patterns on the dialectic materials in volts per meter and the subsequent passive detection of the living human proximate to or traversing a dielectric collector connected to the signal amplifier results from the traversing human with a comparatively high electric field strength in a natural environment with a 1000 fold lower electric field strength. With reference to FIG. 9, the natural environment at 2 meters proximate the ground has an electric field strength of approximately +200 V/m. As previously indicated, the electric field strength of the living human is 180 kV/m. The large differential of the human electric field in the natural environment alters the ambient voltage gradient patterns on the dielectric materials that are proximate to the living human. The method described herein passively detects the changing voltage patterns (or TVG) on the dialectic materials in contact with or proximate to the living human electric field. In the embodiment of the human traversing the carpet collector, the incidence of the traversing human electric field produces a propagating or traveling voltage gradient (TVG) along the surfaces and the interfaces of the dielectric materials proximate. In accordance with well understood dielectric propagation, the lateral gradient waves propagate efficiently where there is a differential in the dielectric constant, in this case air (dielectric constant of 1) and carpet (dielectric constant of 5). The collector, which is in contact with the back of the carpet, is affected by the voltage pattern changes resulting from interfacial polarization and the charge distributions resulting from the incidence and traverse of the living human. In this embodiment, the collector materials have a higher conductivity than the proximate or contact materials, in this case the carpet square. Due to its higher conductivity (lower resistivity), the collector transmits the voltage gradients, which transverse its total geometric area.

In an embodiment of the method with the collector proximate to the human as in the case where C1 dominates (see FIG. 2), the physiological function of the living human can be detected and analyzed.

Figure 10:
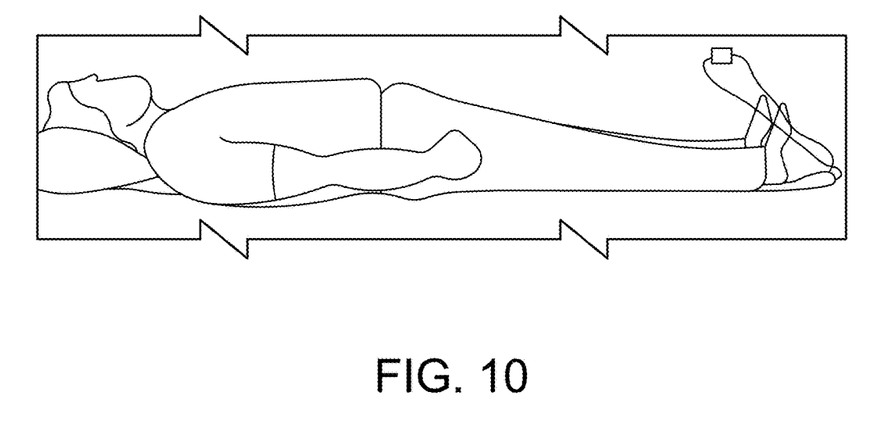
FIG. 10 shows a scenario with the human lying on the collector.

In variations of the embodiment, the collector may be placed on a bed or platform with the human lying on the collector (FIG. 10), data collected in the prone position is comparable to sitting (FIG. 11) which is presented graphically. Or, a human may sit in a chair with the collector placed between the back of the human (FIG. 11) and the back of the chair. Intervening materials such as clothing, bed sheets, etc. do not interfere.

Figure 11:
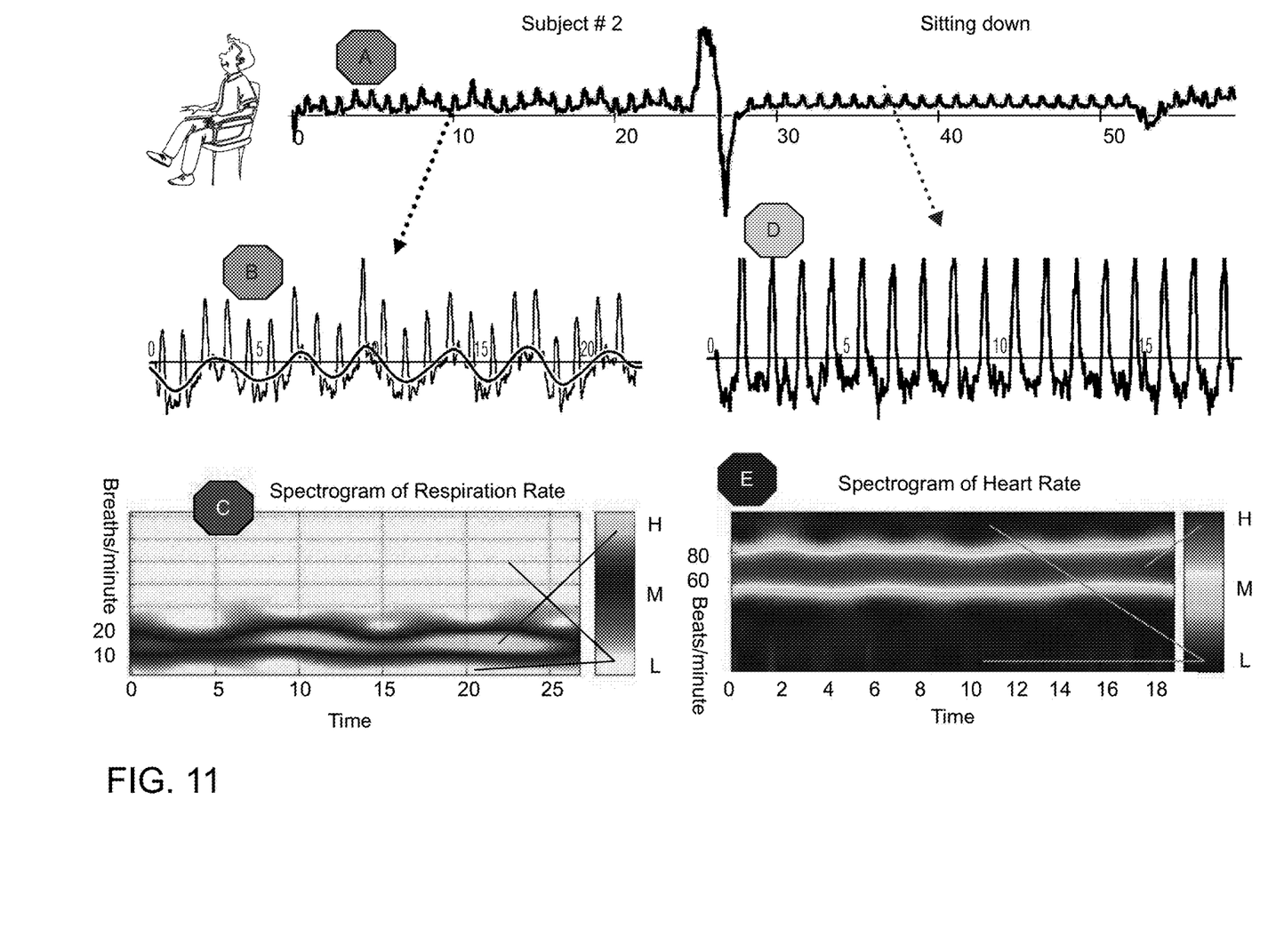
FIG. 11 shows a scenario with the collector placed between the back of the human and the back of the chair and data collected.

The voltage pattern in FIG. 11 is of a human sitting in a chair. The collector is placed between the back of the human and the chair. For Display [A] the first 25 seconds, the subject breathes normally. Note the smooth undulations which represent normal breathing (~3 sec). In the second part of the record, the subject takes a deep breath and holds his breath for about 25 seconds. During both parts of the test period, the sharp spikes represent the heart beating (~1.2 sec).

In the voltage display [B], the display is smoothed out to accentuate the undulating respiration pattern, using, for example, a 60-point, zero-phase, low-pass filter. In display [C], a spectrogram was generated for the respiration data by applying multiple, overlapping, short-term, hamming windowed FFTs to the data (see Tukey method). Respiration appears as a (light) blue line at about 12-15 breaths/minute. In display [D], the period in which the subject held his breath, the heart-rate could be examined independent of the respiration rate. In display [E], a spectrogram was generated for the heart-rate data (as in [C]). Heart-rate appears as a red line. This would be useful in any environment where a sitting human's movements, heart and respiration rates were found valuable to monitor.

Figure 12:
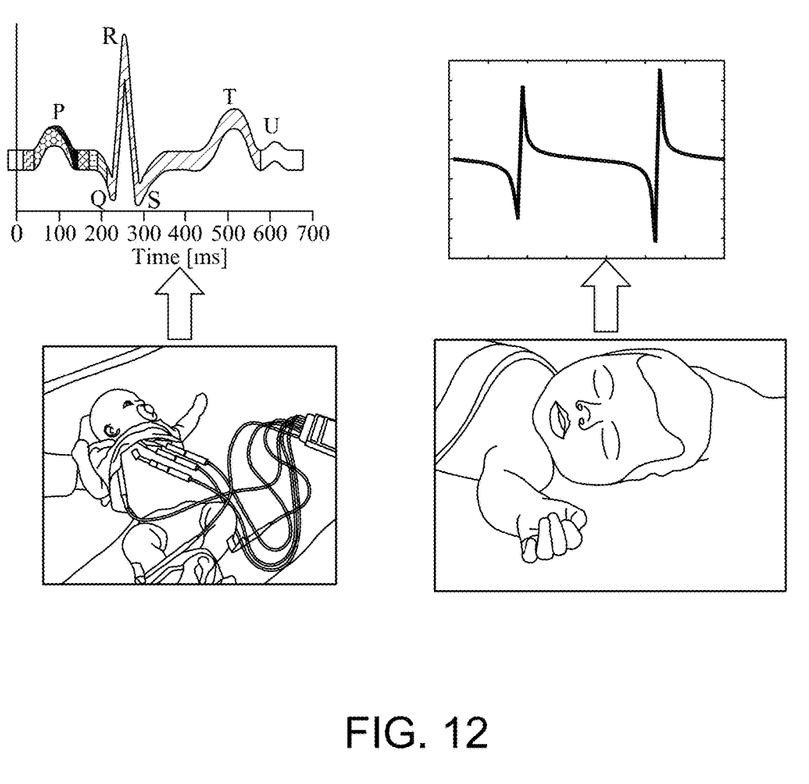
FIG. 12 shows a scenario where the collector is placed beneath the sheets of infant as compared to conventional ECG.

In another embodiment, with reference to FIG. 12, the collector is placed beneath the sheets of an infant. In contrast to the traditional electrocardiogram (ECG), the passive, non-contact monitoring of the physiological electric field is conducted without the danger of entangling the infant in the leads of the contact ECG. The method can control any type of alert system to indicate that the physiological function of the infant transitions above or below a set threshold. This would be useful in any environment where a prone human's movements, heart and respiration rates were found valuable to monitor.

In a preferred embodiment, the input data may be separated into three signals: movement, respiration and heart rate and displayed. The determination of movement, respiration rate and heart rate is the purpose of signal separation. The input signal is separated into time segments. The movement portion of the input date may be transformed to optimize the signal and displayed separately, then removed from the input signal.

Respiration rate and heart rate are determined by transforming the sample data into the frequency domain. Respiration rate is determined by analyzing the above described frequency scan. The lower frequency band of the frequency scan is used to determine the respiration rate. Heart rate in a similar manner may be determined by analyzing the higher frequency band of the frequency scan used to determine the respiration and heart rate.

Following the analyses of each scan, the resulting rates are accumulated and displayed at or near real time. This would be useful in any environment where a human's movements, heart and respiration rates were found valuable to monitor.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A method of detecting a presence or traverse of a living human, comprising:
   (a) monitoring spatial dynamics of a polarized entity including tissue, organs and a living body of the living human;
   (b) filtering extraneous ambient electromagnetic background noise;
   (c) detecting and quantifying amplitude changes in volts per meter per second or current; and
   (d) outputting voltage or current amplitude signals,
   wherein steps (a) and (b) are practiced by connecting a current amplifier having a low frequency voltage spectral density curve to dielectric materials which are proximate to or in contact with the living human or in contact with intervening dielectric materials proximate to or in direct contact with the living human.

2. A method according to claim 1, wherein step (c) is practiced by identifying a response to frequency changes in a volts per meter pattern on the intervening dielectric materials or the proximate/contact dielectric materials.

3. A method according to claim 2, wherein step (c) is further practiced by characterizing the frequency changes in the volts per meter pattern and resetting and responding to a succeeding voltage pattern change.

4. A method of detecting a presence or traverse of a living human, comprising:
   (a) monitoring spatial dynamics of a polarized entity including tissue, organs and a living body of the living human;
   (b) filtering extraneous ambient electromagnetic background noise;
   (c) detecting and quantifying amplitude changes in volts per meter per second or current;
   (d) outputting voltage or current amplitude signals;
   (e) detecting the presence of the living human based on the voltage amplitude signals output in step (d); and
   (f) distinguishing the presence of the living human from a presence of a non-human living entity based on the voltage amplitude signals output in step (d).

5. A method according to claim 4, further comprising detecting a traverse direction based on a pattern of the voltage amplitude signals output in step (d).

6. A method according to claim 4, further comprising detecting a speed of travel.

7. A method of detecting a presence or traverse of a living human, comprising:
   (a) monitoring spatial dynamics of a polarized entity including tissue, organs and a living body of the living human;
   (b) filtering extraneous ambient electromagnetic background noise;
   (c) detecting and quantifying amplitude changes in volts per meter per second or current;
   (d) outputting voltage or current amplitude signals; and
   (e) categorizing the voltage amplitude signals according to the living human and a non-human living entity.

8. A method according to claim 7, wherein the categorizing step comprises:
   generating a plurality of discriminators using empirical data that spans the types of data to be detected; and
   applying the discriminators as templates or filters to the voltage amplitude signals output in step (d), thereby yielding output corresponding to a degree to which the voltage amplitude signals correlate with each of the discriminators.

9. A method of detecting a presence or traverse of a living human, comprising:
   (a) monitoring spatial dynamics of a polarized entity including tissue, organs and a living body of the living human;
   (b) filtering extraneous ambient electromagnetic background noise;
   (c) detecting and quantifying amplitude changes in volts per meter per second or current; and
   (d) outputting voltage or current amplitude signals,
   wherein steps (a) and (b) are practiced by connecting a current amplifier having a low frequency voltage spectral density curve to dielectric materials which are proximate to or in contact with the living human, the method further comprising detecting and analyzing a physiological function of the living human.

10. A method according to claim 9, wherein the physiological function comprises heart and respiration rates.

11. A method according to claim 9, further comprising comparing the physiological function to a threshold value, and generating an alert when the physiological function deviates from the threshold value by a predetermined amount.

12. A sensor for detecting a presence or traverse of a living human by monitoring spatial dynamics of a polarized entity including tissue, organs and a living body of the living human, the sensor comprising:
- a low frequency bandpass filter that filters extraneous ambient electromagnetic background noise from the spatial dynamics of the polarized entity;
- a low current amplifier that amplifies an analog input from the low frequency bandpass filter;
- dielectric materials connected to the low current amplifier, the dielectric materials being proximate to or in contact with the living human or in contact with intervening dielectric materials proximate to or in direct contact with the living human;
- an A/D converter converting output from the low current amplifier into digital voltage amplitude signals; and
- a circuit that detects and quantifies amplitude changes in volts per meter per second based on the digital voltage amplitude signals.

13. A sensor according to claim 12, wherein the circuit is configured to identify a response to frequency changes in a volts per meter pattern on the intervening dielectric materials or the proximate/contact dielectric materials.

14. A sensor according to claim 12, further comprising a display that displays the amplitude changes.

15. A sensor according to claim 14, wherein the display indicates a system on/off configuration.

16. A sensor according to claim 14, wherein the display indicates movement of the living human.

17. A sensor according to claim 14, wherein the display indicates a presence/absence of the living human.

18. A sensor according to claim 17, wherein the display indicates a direction of the living human transecting the sensor.

19. A sensor according to claim 14, wherein the display indicates the living human transecting the sensor.

20. A sensor according to claim 14, wherein the display indicates a direction of the living human transecting the sensor.

21. A sensor according to claim 14, wherein the display indicates a determination of respiration of the living human in a frequency band associated with human respiration.

22. A sensor according to claim 21, wherein the display indicates a respiration rate of the living human in the frequency band associated with human respiration.

23. A sensor according to claim 14, wherein the display indicates a determination of heart activity of the living human in a frequency band associated with human respiration.

24. A sensor according to claim 23, wherein the display indicates a heart rate of the living human in a frequency band associated with human respiration.

25. A sensor according to claim 14, wherein the display indicates bio-chemical or physiological changes of the living human.

26. A method for processing information signals representative of human, or other objects, derived from one or more dielectric collectors, the method comprising:
(a) processing said information signals to determine proximity to, or transition over said dielectric collectors by the human or other object; and
(b) identifying the human or other object as belonging to one or more classes of reference signals, wherein the classes of reference signals include at least one of human specific signals, various non-human specific signals and other inanimate signals, and wherein the classes of reference signals also include signals passing along one or more of said dielectric collectors, crossing over the dielectric collectors, and transiting over the dielectric collectors.

27. A method according to claim 26, wherein the classes of reference signals are determined using à priori signals, wherein features of the à priori signals are compiled to be representative of the classes of reference signals, and wherein the information signals and the à priori signals are transformed to allow the signals and the classes of reference signals to be analyzed and compared in a comparable format.

28. A method according to claim 27, wherein the à priori signals representative of the classes of reference data is compiled and numerically processed to form templates for comparison to the information signals, wherein an autocorrelation function of the information signals is compared with autocorrelation functions of the classes of reference signals.

29. A method according to claim 26, wherein a comparison between the information signals and the reference signals is in terms of correlation coefficients between the information signals and the reference signals.

30. A method according to claim 26, wherein a comparison between the information signals and the reference signals is in terms of a cosine theta between normalized information signals and normalized reference signals.

31. A method according to claim 26, wherein a comparison between the information signals and the reference signals is in terms of a Euclidian distance between the information signals and the reference signals.

32. A method according to claim 26, wherein a comparison between the information signals and the reference signals is in terms of a Mahalanobis distance between the information signals and the reference signals.

* * * * *